(12) United States Patent
Otomaru et al.

(10) Patent No.: US 10,408,776 B2
(45) Date of Patent: Sep. 10, 2019

(54) SENSOR BOARD, LEAD-BEARING SENSOR BOARD, AND SENSOR DEVICE

(71) Applicant: KYOCERA Corporation, Kyoto-shi, Kyoto (JP)

(72) Inventors: Hidekazu Otomaru, Kyoto (JP); Takashi Kimura, Kyoto (JP)

(73) Assignee: Kyocera Corporation, Kyoto-Shi, Kyoto (JP)

( * ) Notice: Subject to any disclaimer, the term of this patent is extended or adjusted under 35 U.S.C. 154(b) by 0 days.

(21) Appl. No.: 15/319,881

(22) PCT Filed: Aug. 22, 2015

(86) PCT No.: PCT/JP2015/073637
§ 371 (c)(1),
(2) Date: Dec. 19, 2016

(87) PCT Pub. No.: WO2016/031739
PCT Pub. Date: Mar. 3, 2016

(65) Prior Publication Data
US 2017/0138877 A1    May 18, 2017

(30) Foreign Application Priority Data

Aug. 29, 2014  (JP) ................................ 2014-175766
Dec. 16, 2014  (JP) ................................ 2014-254181

(51) Int. Cl.
*G01N 27/04*  (2006.01)
*G01N 15/06*  (2006.01)
(Continued)

(52) U.S. Cl.
CPC ............ *G01N 27/04* (2013.01); *G01N 15/06* (2013.01); *G01N 15/0606* (2013.01);
(Continued)

(58) Field of Classification Search
CPC ............... G01N 27/04; G01N 15/0656; G01N 15/0606; G01N 15/06; G01N 2015/0046; G01M 15/102
See application file for complete search history.

(56) References Cited

U.S. PATENT DOCUMENTS 4,307,061 A     12/1981  Sarholz
5,296,122 A *   3/1994   Katsube ................. C23C 14/12
                                                204/192.11
(Continued)

FOREIGN PATENT DOCUMENTS

EP     2090879 A2     8/2009
JP     55-030690 A    3/1980
(Continued)

OTHER PUBLICATIONS

International Search Report, PCT/JP2015/073637, dated Nov. 24, 2015, 2 pgs.

*Primary Examiner* — Akm Zakaria
(74) *Attorney, Agent, or Firm* — Volpe and Koenig, P.C.

(57) ABSTRACT

A sensor board includes: an insulating substrate having a principal surface; and a detecting electrode disposed on the principal surface of the insulating substrate, the detecting electrode being formed mainly of a first metallic material composed of a base-metal based material which is catalytically inactive with respect to a decomposition reaction of particulates, an exposed surface of the detecting electrode being covered by a passivation film of the first metallic material.

8 Claims, 4 Drawing Sheets

(51) Int. Cl.
   *G01M 15/10*        (2006.01)
   *G01N 15/00*        (2006.01)

(52) U.S. Cl.
   CPC ....... *G01N 15/0656* (2013.01); *G01M 15/102* (2013.01); *G01N 2015/0046* (2013.01)

(56) References Cited

U.S. PATENT DOCUMENTS

| | | | |
|---|---|---|---|
| 2002/0142478 A1* | 10/2002 | Wado | G01N 27/124 436/151 |
| 2009/0091340 A1* | 4/2009 | Kim | G01R 27/2623 324/722 |
| 2009/0126458 A1 | 5/2009 | Fleischer et al. | |
| 2009/0315093 A1* | 12/2009 | Li | C23C 16/32 257/314 |
| 2010/0000863 A1 | 1/2010 | Kondo et al. | |
| 2011/0260219 A1 | 10/2011 | Wahl et al. | |
| 2014/0285976 A1* | 9/2014 | Kobayashi | H05K 3/04 361/736 |

FOREIGN PATENT DOCUMENTS

| | | |
|---|---|---|
| JP | 59-197847 A | 11/1984 |
| JP | 2008-547032 A | 12/2008 |
| JP | 2010-032488 A | 2/2010 |
| JP | 2012-503171 A | 2/2012 |
| JP | 2012-150937 A | 8/2012 |
| WO | 2012/162685 A1 | 11/2012 |

* cited by examiner

SENSOR BOARD, LEAD-BEARING SENSOR BOARD, AND SENSOR DEVICE

TECHNICAL FIELD

The present invention relates to a sensor board including a detecting electrode, a lead-bearing sensor board, and a sensor device.

BACKGROUND ART

As a sensor board used for an exhaust gas sensor or the like, there is employed a sensor board including an insulating substrate formed of a ceramic sintered compact such as an aluminum oxide sintered body, and a detecting electrode disposed on a surface of the insulating substrate. For example, in association with adhesion of a to-be-detected substance contained in the exhaust gas to the detecting electrode, change in the resistance or the current value of the detecting electrode is caused by a decrease in the electric insulation relative to adjacent another detecting electrode. Thus, on the basis of this change in the resistance or the current value, the content of the to-be-detected substance in the exhaust gas or the like is calculated and detected.

As the material used for forming the detecting electrode, platinum is widely employed which is a metallic material less prone to be oxidized even at a high temperature of the exhaust gas or the like.

CITATION LIST

Patent Literature

Patent Literature 1: Japanese Unexamined Patent Publication JP-A S55-30690 (1980)
Patent Literature 2: Japanese Unexamined Patent Publication JP-A S59-197847 (1984)

SUMMARY OF INVENTION

Technical Problem

Nevertheless, in the case where platinum is employed as a material for the detecting electrode, since platinum has a catalytic action, there has been a possibility of occurrence of the following problem. That is, for example, in the case where the to-be-detected substance is particulates of soot (carbon) or the like which is a substance relatively easily decomposed and removed, the particulates serving as the to-be-detected substance are easily decomposed by the catalytic action of platinum contained in the detecting electrode. The decomposed particulates of soot or the like are easily dispersed to the outside so as to be removed. That is, an amount smaller than that of the particulates having actually adhered to the detecting electrode remains on the detecting electrode and in the periphery of the detecting electrode and then this small amount is detected. Thus, a value smaller than the actual content of soot or the like is detected as the content of soot or the like in the exhaust gas and hence the accuracy of detection is degraded.

Solution to Problem

A sensor board according to an embodiment of the invention includes: an insulating substrate having a principal surface; and a detecting electrode disposed on the principal surface of the insulating substrate, the detecting electrode being formed mainly of a first metallic material composed of a base-metal based material which is catalytically inactive with respect to a decomposition reaction of particulates, an exposed surface of the detecting electrode being covered by a passivation film of the first metallic material.

A sensor device according to an embodiment of the invention includes: the sensor board mentioned above; and a power supply part which supplies a potential to the detecting electrode.

Advantageous Effects of Invention

In the sensor board according to an embodiment of the invention, the detecting electrode has the above-mentioned configuration and hence, for example, does not have a catalytic action with respect to decomposition of soot or the like. Thus, oxidation or the like is less prone to occur in the to-be-detected substance having adhered to the detecting electrode. Further, the exposed surface of the detecting electrode is covered by the passivation film of the first metallic material and hence a possibility of oxidation of the entirety of the detecting electrode is reduced. This realizes a sensor board having a high accuracy of detection.

The sensor device according to an embodiment of the invention includes a sensor board having the above-mentioned configuration and hence has a high accuracy of detection.

DESCRIPTION OF EMBODIMENTS

A sensor board and a sensor device according to embodiments of the invention are described below with reference to the accompanying drawings. Here, the distinction of up and down in the following description is merely for convenience and hence does not limit the up and down orientation in actual use of the sensor board and the like.

First Embodiment

Figure 1:
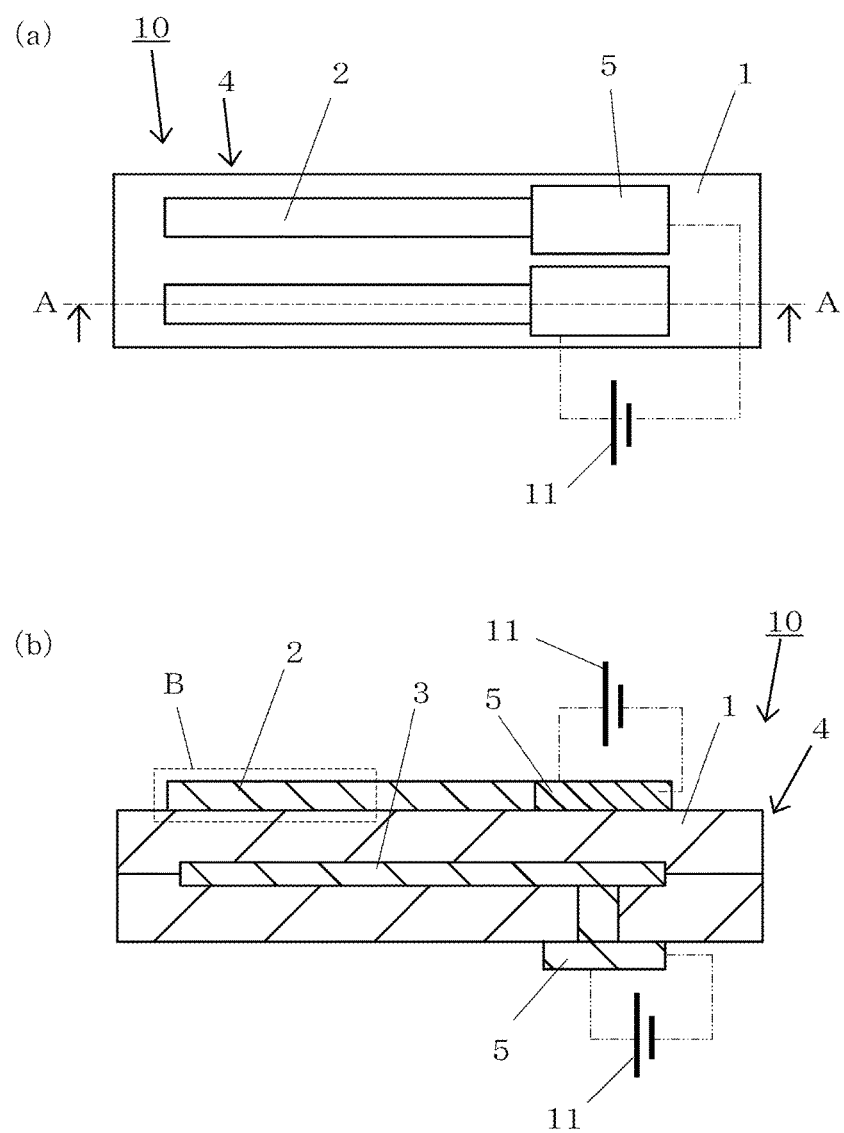
FIG. 1(a) is a top view showing a sensor board and a sensor device according to a first embodiment of the invention.
FIG. 1(b) is a sectional view taken along the line A-A in FIG. 1(a)
Figure 2:
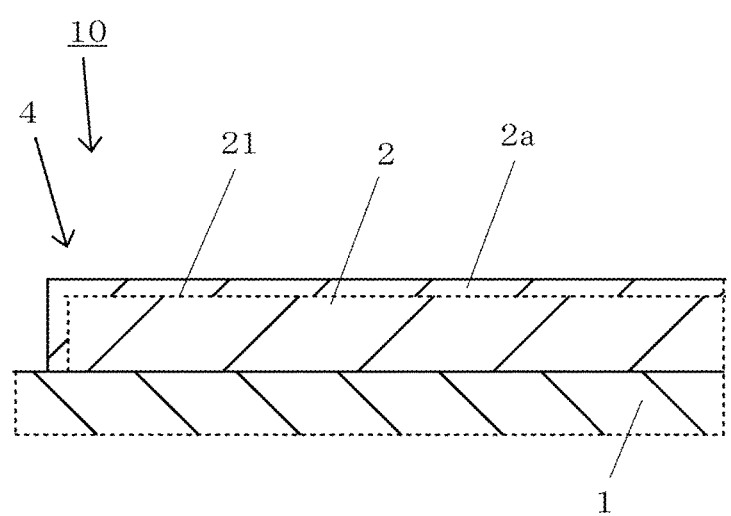
FIG. 2 is a sectional view showing an enlarged B portion of FIG. 1.

FIG. 1(a) is a top view showing a sensor board and a sensor device according to a first embodiment of the invention. FIG. 1(b) is a sectional view taken along the line A-A in FIG. 1(a). Further, FIG. 2 is a sectional view showing an enlarged B portion of FIG. 1. A sensor board 4 of the first embodiment basically comprises: an insulating substrate 1; detecting electrodes 2 disposed on the principal surface (the upper surface in the example of FIG. 1) of the insulating substrate 1; and an internal wiring 3 serving as an electrically conducting path for establishing external connection of each detecting electrode 2. Further, an exposed surface 21 of the detecting electrode 2 is covered by a passivation film 2a.

Here, the exposed surface 21 of the detecting electrode 2 indicates a portion not in contact with the insulating substrate 1 within the surface of the detecting electrode 2.

For example, the insulating substrate 1 is a substrate which has a flat-plate shape such as a quadrangular plate shape and on which the plurality of detecting electrodes 2 are disposed in an electrically insulated manner from each other. For example, the insulating substrate 1 is constructed from a ceramic sintered body such as an aluminum oxide sintered body, an aluminum nitride sintered body, a mullite sintered body, a glass ceramic sintered body, and a zirconia-based ceramic (e.g., a zirconium oxide sintered body). The insulating substrate 1 may be formed by stacking together a plurality of insulating layers (no reference numerals) each composed of such a ceramic sintered body.

For example, in the case where the insulating substrate 1 is to be formed by laminating together a plurality of insulating layers each composed of an aluminum oxide sintered body, the following method can be manufactured. First, a suitable organic binder, a solvent, and the like are added and mixed to raw material powder of aluminum oxide, silicon oxide, magnesium oxide, calcium oxide, or the like, to obtain a slurry mixture (a slurry). Then, the slurry is formed into a sheet shape by a doctor blade method, a calender roll method, or otherwise, to prepare a ceramic green sheet. Then, punching is performed suitably on this ceramic green sheet and then a plurality of sheets prepared by the punching are laminated together when necessary to obtain a stacked body. After that, the stacked body is fired at a high temperature (approximately 1300 to 1600° C.), and thereby the insulating substrate 1 can be obtained.

The detecting electrode 2 is a part for measuring the content of particulates of soot or the like in the environment where the sensor board 4 is located. When particulates of soot or the like adhere to the detecting electrodes 2, the electric insulation varies between the detecting electrodes 2 adjacent to each other. This change in the electric insulation causes change in the electric resistance, the current value, and the like of the detecting electrodes 2. When the change in the electric resistance or the like is detected, the mass of particulates in the environment where the detecting electrodes 2 are located is calculated and detected. From the mass of particulates and the flow rate (the volume) of the gas in the environment where the detecting electrodes 2 are located, the content ratio of particulates in the gas is calculated and detected.

Thus, as a metallic material in which such change in the electric resistance occurs, a first metallic material described later is contained as a main component in the detecting electrode 2. The first metallic material is composed of a base-metal based material which is catalytically inactive with respect to a decomposition reaction of particulates (simply referred to as "catalytically inactive", hereinafter). For example, the particulates are soot (particulates of carbon). Further, the base-metal based material constituting the first metallic material is a material in which a passivation film can be formed on the exposed surface 21 of the detecting electrode 2. Such a base-metal based material may be a base-metal material such as iron, aluminum, nickel, titanium, and chromium.

Further, the base-metal based material may be a material containing silicon in addition to the above-mentioned base-metal material. In this case, the silicon may form a compound (silicide) with the above-mentioned base-metal material. Further, the base-metal based material may be a base-metal material which is other than the above-mentioned base-metal materials and on which a passivation film has been formed by a chemical combination with silicon. For example, such base-metal materials on which a passivation film can be formed by a chemical combination with silicon include molybdenum. In other words, the base-metal based material may be molybdenum silicide.

For example, approximately 80 mass % or more of the first metallic material is contained in the detecting electrode 2 and hence serves as the main component of the detecting electrode 2. In addition to the first metallic material, the detecting electrode 2 may contain an inorganic component such as glass or ceramics. For example, such an inorganic component serves as a component for adjustment of firing shrinkage when the detecting electrodes 2 are formed by co-firing with the insulating substrate 1 as described later.

The environment where the sensor board 4 is located is, for example, an exhaust passage for the exhaust gas of an automobile. When the amount of particulates detected by the sensor board 4 increases, it is detected that the content of particulates flowing through the exhaust passage has increased. By virtue of this, for example, it is possible to detect a fault in a DPF (diesel particulate filter) serving as a filter device for removing particulates of soot or the like from the exhaust gas of a diesel engine.

In order to effectively detect change in the resistance caused by adhesion of particulates, it is preferable that the detecting electrodes 2 are formed in a pattern in which the length of a portion contributing to the detection is easily increased. For example, such patterns include a pattern of comb shape and a linear pattern including a pattern of elongated narrow rectangular shape (belt shape). FIG. 1 shows an example that the detecting electrode 2 is in a pattern of elongated narrow rectangular shape.

The internal wiring 3 is formed in the inside of the insulating substrate 1 and serves as an electrically conducting path, for example, for electrically connecting the detecting electrode 2 on the upper surface of the insulating substrate 1 to a connection pad 5 described later on the lower surface. The internal wiring 3 may include a heater located in the inside of the insulating substrate 1. FIG. 1(b) shows an example that a part of the internal wiring 3 is a heater located in parallel to the principal surface of the insulating substrate 1. For example, the internal wiring 3 serving as the heater is a part for pre-heating the detecting electrode 2. In the case where the detecting electrodes 2 are pre-heated, change in the resistance between the detecting electrodes 2 caused by the adhesion of particulates becomes keener and hence the accuracy of detection of particulates is improved.

Further, for example, the internal wiring 3 may include even a portion (not shown) which is provided so as to extend from the detecting electrode 2 on the upper surface of the insulating substrate 1 toward the other principal surface (the lower surface in the example of FIG. 1) on the opposite side to the principal surface on which the detecting electrode 2 is disposed within the insulating substrate 1. In this case, the detecting electrode 2 is electrically led out to the lower surface of the insulating substrate 1 by the internal wiring 3. Here, the internal wiring 3 may include a penetration conductor (no reference numeral) going through at least part of the thickness direction of the insulating substrate 1. Further, the internal wiring 3 may include an internal wiring conductor (not shown) such as a circuit pattern disposed between insulating layers.

In the sensor board 4 of the first embodiment, a connection pad 5 for external connection is disposed on the upper surface and the lower surface of the insulating substrate 1. The connection pad 5 on the upper surface of the insulating substrate 1 is connected directly to the end part of the detecting electrode 2. In this example, the connection pad 5 is in a pattern of rectangular shape. Then, the length (the width) of the short side is larger than the width of the detecting electrode 2. Since the width of the connection pad 5 is larger than the width of the detecting electrode 2, electrical connection of the detecting electrode 2 to the external electric circuit becomes easy. An external electric circuit (not shown) is electrically connected through this connection pad 5 to the detecting electrode 2. A signal such as change in the electric resistance detected by the detecting electrode 2 is transmitted to the external electric circuit, and then predetermined processing such as the detection of particulates and the display is performed.

Further, the connection pad 5 on the lower surface of the insulating substrate 1 is connected directly to an internal wiring 3 portion electrically led out to the lower surface of the insulating substrate 1. By virtue of this, an electrically conducting path (no reference numeral) is formed that electrically connects the internal wiring 3 and the connection pad 5 to each other. For example, this electrically conducting path is used for electrically connecting the internal wiring 3 serving as a heater, to the external electric circuit. Then, for example, a predetermined electric power is supplied from the external electric circuit to the heater (the internal wiring 3).

When the connection pads 5 on the upper surface and the lower surface of the insulating substrate 1 are respectively joined to predetermined locations of the external electric circuit by using an electrically conductive joining material such as solder or conductive adhesives, the detecting electrodes 2 and the internal wirings 3, and the external electric circuit are electrically connected to each other.

For example, the electrical connection of the connection pads 5 to the external electric circuit is established through an electrically conductive connection material such as solder. Further, a lead terminal (not shown in FIGS. 1 and 2) may be joined in advance to the connection pad 5 and then electrical connection to the external electric circuit may be established through this lead terminal.

In the sensor board 4 of the first embodiment, the surface portion of the detecting electrode 2 does not contain platinum. Thus, for example, a catalytic action with respect to a chemical reaction of the to-be-detected substance such as oxidation of soot or the like is effectively reduced in comparison with a case where platinum is contained. The surface portion of the detecting electrode 2 indicates a portion including the exposed surface 21 of the detecting electrode 2 and the passivation film 2a covering the exposed surface 21. Thus, oxidation or the like is less prone to occur in the to-be-detected substance having adhered to the detecting electrode 2. This realizes the sensor board 4 having a high accuracy of detection.

Further, the exposed surface 21 of the detecting electrode 2 is covered by the passivation film 2a. Thus, a possibility of oxidation of the entirety of the detecting electrode 2 is reduced. This realizes the sensor board 4 having a high accuracy of detection and a high long-term reliability.

Here, as described above, the exposed surface 21 of the detecting electrode 2 indicates a portion which is not in contact with the insulating substrate 1 within the surface of the detecting electrode 2 and which is exposed to the outside when the passivation film 2a is supposedly not present. For example, in the detecting electrode 2 on the inner side relative to the exposed surface 21, the base-metal material contained in the above-mentioned base-metal based material (the first metallic material) is present in the form of a metal (non-oxide).

As described above, the first metallic material contained in the detecting electrode 2 contains at least one kind selected from base-metal materials such as iron, aluminum, nickel, titanium, chromium, and molybdenum on which the passivation film 2a can easily be formed. Further, a compound (silicide) between such a base-metal material and silicon may be contained. Such a base-metal based material is catalytically inactive and does not have a catalytic action with respect to the decomposition of particulates or the like. The detecting electrode 2 contains the first metallic material composed of such a base-metal based material, as the main component at a ratio of approximately 80 mass % or more.

The detecting electrode 2 may contain another metallic component in addition to the first metallic material serving as the main component. Further, this another metallic material need not necessarily be a metallic material on which the passivation film 2a can easily be formed. That is, any other metallic material (such as tungsten) may be employed.

For example, the detecting electrode 2 is formed by the following method. That is, powder of the above-mentioned base-metal based material is mixed and kneaded together with an organic solvent and a binder so that metal paste is prepared. Then, the metal paste is applied into a predetermined pattern on the principal surface or the like of the ceramic green sheet constituting the insulating substrate 1. For example, the application of the metal paste is performed by screen printing. After that, co-firing is performed on the metal paste and the ceramic green sheet. As a result the above-mentioned process, the insulating substrate 1 provided with the detecting electrodes 2 is obtained.

For example, the thickness of the passivation film 2a is set to be about 0.1 to 5 μm. When the thickness is at this level, the exposed surface 21 of the detecting electrode 2 is effectively covered by the passivation film 2a. Thus, a possibility is effectively reduced that the entirety or the major part of the detecting electrode 2 is oxidized.

As long as the thickness of the passivation film 2a is uniform over the entirety of the exposed surface 21 of the detecting electrode 2, the progression of oxidation to the inside can be suppressed uniformly over the entirety of the detecting electrode 2. Such a uniform thickness in this case indicates a situation that a fluctuation in the thickness of the passivation film 2a in one detecting electrode 2 falls within ±10% of the median of the thickness. That is, for example, in the case where the median of the thickness of the passivation film 2a is approximately 2 μm, a situation is indicated that the thickness values fall within a range of approximately 1.8 to 2.2 μm.

In the exposed surface 21 of the detecting electrode 2, the entire surface need not necessarily be covered by the passivation film 2a. For example, in terms of the area ratio, it is sufficient that approximately 90% of the exposed surface 21 of the detecting electrode 2 is covered by the passivation film 2a. In other words, it is sufficient that 90% or more of the surface portion of the detecting electrode 2 is composed of the passivation film 2a. When the exposed surface 21 of the detecting electrode 2 is covered by the passivation film 2a at a ratio of this level, a possibility of progression of oxidation of the entirety of the detecting electrode 2 is effectively reduced.

Here, in the exposed surface 21 of the detecting electrode 2, in order to more effectively suppressing the oxidation or the like of the detecting electrode 2, it is preferable that the entire surface is covered by the passivation film 2a. In other words, when the entire surface of the exposed surface 21 of the detecting electrode 2 is covered by the passivation film 2a, the following advantage is obtained. That is, in this case, the possibility of progression of oxidation of the entirety of the detecting electrode 2 is more effectively reduced.

Here, when the passivation film 2a is excessively thick, the initial resistance of the surface portion of the detecting electrode 2 (the resistance before the device is placed in an environment including particulates) becomes high. Thus, the conduction resistance between the detecting electrode 2 (the sensor board 4) and the external electric circuit increases and hence change in the resistance of the detecting electrode 2 caused by the adhesion of particulates becomes hard to be detected.

When the passivation film 2a is to be formed on the exposed surface 21 of the detecting electrode 2, for example, it is sufficient that the above-mentioned firing is performed in an atmosphere containing a minute amount of oxygen and water. Then, at the time of firing, the passivation film 2a is generated on the exposed surface 21 of the metallic material containing the base-metal based material. Alternatively, it is sufficient that after the formation of the detecting electrode 2 performed by using the above-mentioned metallic material, the sensor board 4 including the detecting electrode 2 is thermally treated in an environment including a minute amount of oxygen and water. As a result of this thermal treatment, the exposed surface portion of the metallic material is oxidized so that the passivation film 2a is generated.

In general, in such a firing process for the sensor board 4, a non-oxidizing atmosphere such as a reducing atmosphere or an inert atmosphere is employed. Nevertheless, in the firing in such a non-oxidizing atmosphere, the passivation film 2a is not effectively formed. In contrast, when the firing condition of the atmosphere or the like is set up as described above, the passivation film 2a can effectively be formed.

For example, in the case where the detecting electrode 2 contains an iron-nickel-chrome alloy as the main component, the passivation film 2a is an oxide layer containing at least one kind selected from iron oxide, chromium oxide, and chromium oxide. Since the exposed surface 21 of the detecting electrode 2 is covered by the passivation film 2a as described here, a situation is suppressed that the oxidation progresses even to the iron-nickel-chrome alloy located on the inner side relative to the exposed surface 21 of the detecting electrode 2.

The first metallic material constituting the passivation film 2a may be composed mainly of an iron-nickel-chrome alloy. That is, the base-metal based material may be an iron-nickel-chrome alloy. In this case, in addition to the iron-nickel-chrome alloy serving as the main component, the first metallic material may contain another base-metal material such as titanium or aluminum at a ratio of approximately 10 mass % or less.

In this case, the following advantage is obtained. That is, the passivation film 2a in this case is formed by oxidation of a metallic material containing iron, nickel, and chromium. For this purpose, the first metallic material serving as the main component of the detecting electrode 2 contains iron, nickel, and chromium. For example, when such a metallic material as iron in the form of a metal paste as described above is employed in the co-firing with the insulating substrate 1 (a ceramic green sheet), the detecting electrode 2 can easily be formed. Further, the formation of the passivation film 2a is easy and the progression of oxidation to the inside (the inner side) of the detecting electrode 2 is also more effectively suppressed. Further, such a base-metal material is a catalytically-inactive metal having no catalytic action.

Thus, when the easiness of formation of the passivation film 2a and further the measurement accuracy, the reliability, and the productivity as the sensor board 4 are taken into consideration, it is more advantageous that an alloy material composed mainly of an iron-nickel-chrome alloy is employed as the first metallic material.

A detailed composition of the first metallic material composed of an iron-nickel-chrome alloy which is a base-metal based material is, for example, 1 to 55 mass % of iron (Fe), 20 to 80 mass % of nickel (Ni), 10 to 25 mass % of chromium (Cr), 0.1 to 5 mass % of titanium (Ti), and 0.1 to 5 mass % of aluminum (Al).

Further, there may be employed another example that the content of nickel is relatively high. In this case, the composition of the first metallic material is, for example, 6 to 10 mass % of iron, approximately 73 mass % or more of nickel, and 14 to 17 mass % of chromium. Further, there may be employed yet another example that the content of chromium is as high as the order of the content of nickel. In this case, the composition of the first metallic material is, for example, approximately 41 mass % or more of iron, 30 to 30.5 mass % of nickel, and 30 to 35.5 mass % of chromium.

Further, in each example given above in which the first metallic material is an iron-nickel-chrome alloy, the detecting electrode 2 may further contain a minute amount of base-metal material such as manganese or aluminum. Further, a minute amount of metallic material such as copper which is not a base-metal material may further be contained. Further, a minute amount of non-metallic substance such as carbon, sulfur, or silicon may further be contained.

Further, the first metallic material may be composed mainly of iron and chromium. Also in this case, in addition to the iron-chrome alloy serving as the main component, the first metallic material may contain another base-metal material such as titanium or aluminum at a ratio of approximately 10 mass % or less.

Also in this case, the passivation film 2a containing such a base-metal based material is formed by oxidation of the metallic material containing iron and chromium. Thus, the metallic material contained in the detecting electrode 2 is set to contain iron and chromium. Also in this metallic material, when the metallic material in the form of a metal paste is employed, the detecting electrode 2 can easily be formed by co-firing with the insulating substrate 1. Further, the formation of the passivation film 2a is easy and the progression of oxidation to the inside (the inner side) of the detecting electrode 2 is also more effectively suppressed. Further, such a base metal is a catalytically-inactive metal having no catalytic action.

Thus, when the easiness of formation of the passivation film 2a and further the measurement accuracy, the reliability, and the productivity as the sensor board 4 are taken into consideration, the first metallic material may be an alloy material composed mainly of iron-chromium. Here, the iron-chromium alloy may be regarded as a material obtained by removing the nickel component from the iron-nickel-chrome alloy described above. Passivation in the iron-chromium alloy is easier than in the iron-nickel-chrome alloy. Thus, formation of the passivation film 2a on the surface portion of the detecting electrode 2 becomes easier. For example, the composition of the iron-chromium alloy is 70 to 80 mass % of iron and 20 to 30 mass % of chromium. Further, in the case where the first metallic material further contains another base-metal material such as aluminum, the composition is, for example, 70 to 75 mass % of iron, 20 to 25 mass % of chromium, and 3 to 7 mass % of aluminum.

Here, it is sufficient that the passivation film 2a covers the exposed surface 21 of the detecting electrode 2 as shown in FIG. 2. The passivation film 2a may be not provided in a portion in contact with the insulating substrate 1 within the surface of the detecting electrode 2.

Further, when the passivation film 2a is not provided in a portion in contact with the internal wiring 3 within the surface of the detecting electrode 2, the contact resistance between the detecting electrode 2 and the internal wiring 3 is easily suppressed low. In this case, the internal wiring 3 is realized so as to have an advantageous configuration in the point of improvement of the electrical characteristics as the sensor board 4.

For example, the passivation film 2a can be detected by cutting the sensor board 4 at a portion where the detecting electrode 2 is provided, in such a manner that a longitudinal sectional view is obtained, and then by analyzing the surface portion of the detecting electrode 2 by a method such as electron probe microanalyzer (EPMA) analysis or X-ray diffraction analysis. Further, the thickness of the passivation film 2a can also be measured by this method.

Similarly to the detecting electrode 2, for example, the internal wiring 3 may be composed mainly of the first metallic material, and the surface thereof may be provided with a passivation film (not shown) of the first metallic material. Further, the internal wiring 3 may be composed of a metal less prone to be oxidized such as platinum or gold.

Further, for example, the connection pad 5 also may be prepared by using a metallic material similar to that of the detecting electrode 2 by a similar method. However, in the case where the detecting electrodes 2 and the periphery thereof (e.g., the upper surface alone of the insulating substrate 1) within the sensor board 4 are solely exposed to the inside of the passage of a gas containing particulates or the like, the connection pad 5 may not contain a base-metal based material on which the above-mentioned passivation film can easily be formed. That is, in such a case, since a possibility that the connection pad 5 is oxidized by a high temperature gas or the like is small, the connection pad 5 need not necessarily have oxidation resistance similar to that of the detecting electrode 2.

Further, the internal wiring 3 and the connection pad 5 are not a part for detecting particulates of soot or the like serving as a to-be-detected substance and hence may be composed of a metallic material having a catalytic action or, alternatively, may be composed of any other metallic material. That is, for example, the internal wiring 3 and the connection pad 5 may be formed of tungsten, manganese, cobalt, copper, gold, or an alloy (such as a nickel-cobalt alloy) containing such a metallic material. For example, when the ease of formation by the co-firing with the insulating substrate 1 formed of an aluminum oxide sintered body, the strength of joining to the insulating substrate 1, and the characteristics such as the electric resistance are taken into consideration, the internal wiring 3 and the connection pad 5 may be formed of a material containing tungsten as the main component.

Further, a plating layer (not shown) of nickel, gold, or the like may be cover the exposed surface of the connection pad 5. For example, providing with the plating layer makes it possible to suppress oxidation or corrosion in the connection pad 5, and improve the characteristics such as the wettability of solder for connection of the connection pad 5 to the external electric circuit. This improves the reliability or the like as the sensor board 4.

Further, the first metallic material constituting the detecting electrode 2 may be a base-metal based material composed mainly of molybdenum silicide (such as $MoSi_2$). In this case, molybdenum silicide is a base-metal based material. Further, in this case, the first metallic material may contain another base-metal material such as iron and nickel in addition to molybdenum silicide. Further, the first metallic material may contain an iron-nickel-chrome alloy and molybdenum silicide as the main components.

In this case, for example, in the case where the glass component described above is contained in the detecting electrode 2, the glass component is less prone to enter a space between the iron-nickel-chromium particles and the molybdenum silicide particles. Thus, over-sintering caused by the entering of the glass component into a space between these particles is less prone to occur. This permits further improvement of the oxidation resistance of the detecting electrode 2.

For example, in the case where the detecting electrode 2 contains molybdenum silicide, the content is set to be approximately 90 to 100 mass %. By virtue of this, the above-mentioned effect is more reliably achieved.

Second Embodiment

Figure 3:
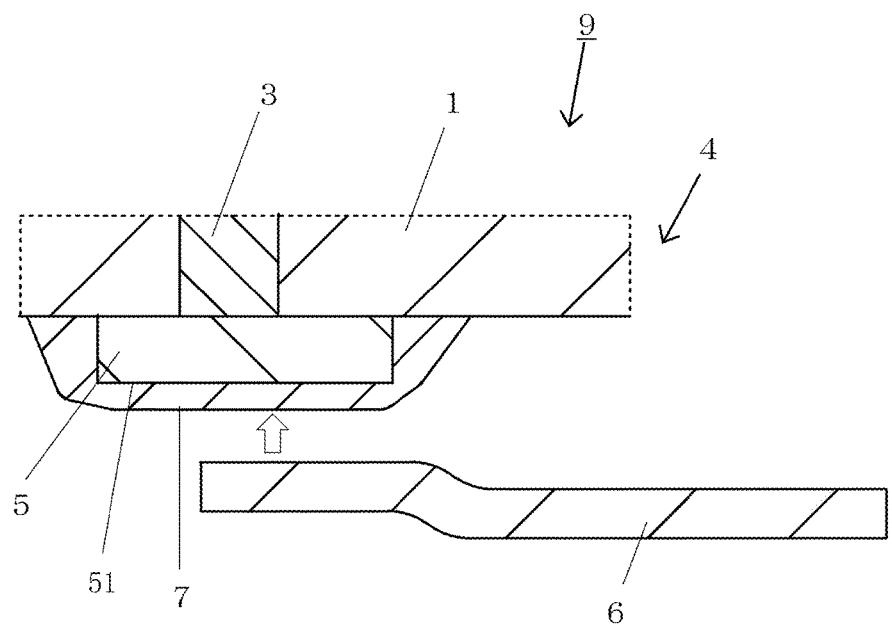
FIG. 3 is a sectional view showing an enlarged main part of the sensor board and the lead-bearing sensor board according to a second embodiment of the invention.

FIG. 3 is a sectional view showing the main part of the sensor board 4 according to a second embodiment. This main part corresponds to the connection pad 5 of the sensor board 4 according to the first embodiment and the periphery thereof. In FIG. 3, like parts to those in FIG. 1 are designated by like reference numerals. Here, in FIG. 3, the connection pad 5 on the lower surface side of the insulating substrate 1 is adopted as an example. However, the following description holds similarly also for the connection pad 5 on the upper surface of the insulating substrate 1.

As for the other part except for the main part, the sensor board 4 according to the second embodiment is similar to the sensor board 4 according to the first embodiment. Description is omitted for the matters similar to those of the first embodiment.

In the second embodiment, the first metallic material is composed mainly of an iron-nickel-chrome alloy or, alternatively, composed mainly of an iron-chromium alloy. Also in this case, the first metallic material may contain another base-metal based material such as titanium. Further, the connection pad 5 is formed of the same metallic material as the detecting electrode 2. That is, the connection pad 5 is formed mainly of the first metallic material composed of a base-metal based material composed mainly of an iron-chrome based alloy like an iron-nickel-chrome alloy and an iron-chromium alloy. Further, a lead terminal 6 is located so as to be electrically connected to the connection pad 5. The lead terminal 6 is joined to the connection pad 5 via a joining layer 7. Here, the joining layer 7 is provided on at least part of the exposed surface 51 of the connection pad 5. Details of the lead terminal 6 and a lead-bearing sensor board 9 including the lead terminal 6 and the sensor board 4 are described later. Here, in FIG. 3, the lead terminal 6 and the sensor board 4 are shown separately from each other. The lead terminal 6 is positioned in the direction indicated by an arrow in the figure and then joined to the connection pad 5.

The joining layer 7 is formed of a second metallic material containing as the main component the same metallic material as the connection pad 5 and further containing at least one of aluminum and silicon as an additive material. In this case, the connection pad 5 is formed of the same metallic material as the detecting electrode 2. The detecting electrode 2 is formed mainly of the first metallic material composed of an iron-nickel-chrome alloy or an iron-chromium alloy.

That is, the joining layer 7 is formed of the second metallic material obtained when at least one of aluminum and silicon is added to an iron-chrome based alloy (the first metallic material) such as an iron-nickel-chrome alloy or an iron-chromium alloy. The aluminum and the silicon serve as an additive material for making the melting temperature of the second metallic material lower than the first metallic material. By virtue of the additive material, the second metallic material constituting the joining layer 7 has a lower melting temperature than the first metallic material.

Thus, when the lead terminal 6 is to be joined onto the connection pad 5, the joining layer 7 alone can be melted without melting of the connection pad 5. By virtue of this, the lead terminal 6 can easily be joined to the connection pad 5.

Further, a possibility is reduced that the connection pad 5 or the like is partly melted at the time of joining of the lead terminal 6. Thus, the pattern of the connection pad 5 can easily be maintained in the predetermined shape.

Further, in the case where the detecting electrode 2 is formed of the same metallic material as the connection pad 5, pattern deformation caused by the partial melting of the detecting electrode 2 or the like at the time of joining of the lead terminal 6 can effectively be suppressed. Further, degradation or the like of the electric insulation between the detecting electrodes 2 caused by the pattern deformation can be suppressed.

Here, for example, the connection pad 5 may be formed mainly of an iron-chromium alloy and may contain approximately 0.1 to 5 mass of aluminum. That is, a component corresponding to the additive material in the joining layer 7 may be contained in the connection pad 5. In such a case, it is sufficient that the content ratio of the additive material such as aluminum in the joining layer 7 is set higher than the content ratio of aluminum or the like in the connection pad 5 by approximately 0.1 to 5.0 mass %.

In a specific example, in the case where the detecting electrode 2 and the connection pad 5 are both formed mainly of the first metallic material composed of an iron-chromium-aluminum alloy and that the content ratio of aluminum is approximately 5 mass %, the joining layer 7 is formed of the second metallic material obtained when 5 mass % of aluminum is outside-added to 100 mass parts of the iron-chromium-aluminum alloy. At that time, the detecting electrode 2 and the connection pad 5 both have a melting temperature of approximately 1550° C. In contrast, the joining layer 7 has a melting temperature of approximately 1450° C. Thus, it is sufficient that the brazing temperature (e.g., the peak temperature) for the lead terminal 6 is set to be approximately 1480° C.

For example, the content ratio of the additive material in the second metallic material is approximately 0.1 to 5.0 mass parts in outside addition relative to the 100 mass parts of the iron-chrome based alloy serving as the main component. In the case where the content ratio of the additive material is at the above-mentioned level, the melting temperature of the joining layer 7 can effectively be made lower than the melting temperature of the connection pad 5 composed of the first metallic material.

The joining layer 7 may be provided so as to extend from the exposed surface 51 of the connection pad 5 to the principal surface of the insulating substrate 1. In other words, the joining layer 7 may continuously cover a portion extending from the principal surface of the insulating substrate 1 to the exposed surface 51 (e.g., the side surfaces and the upper surface) of the connection pad 5. The joining layer 7 may continuously cover the entire surface extending from the principal surface of the insulating substrate 1 to the exposed surface 51 of the connection pad 5.

In this case, the aluminum and the silicon serving as the additive material of the joining layer 7 are active materials and hence easily react with the alumina or the glass component of the insulating substrate 1 and have a high chemical affinity to each other. Thus, the joining layer 7 and the insulating substrate 1 are more firmly joined together. Thus, this configuration is more effective in the improvement of the strength of the lead terminal 6 and the connection pad 5 via the joining layer 7.

Here, aluminum has a higher activity of joining to the insulating substrate 1 formed of an aluminum oxide sintered body or the like, than silicon. Thus, in the case where the joining layer 7 is provided so as to extend to the principal surface of the insulating substrate 1, aluminum is more preferable as the additive material from the perspective of the above-mentioned improvement of the strength of joining to the insulating substrate 1.

(Sensor Device)

For example, a sensor device 10 of the embodiment is configured by: the sensor board 4 of the first or the second embodiment; and a power supply part 11 for supplying a potential to the detecting electrode 2. The following description is given for an example that the sensor device 10 is constructed such that the power supply part 11 is electrically connected to the sensor board 4 according to the first embodiment. Also in the case where the sensor board 4 according to the second embodiment is employed, a sensor device 10 having a similar effect as the following example can be prepared by a similar method.

The electrodes (such as the positive electrode and the negative electrode) different from each other in the power supply part 11 are connected to the lead terminals 6 different from each other. In the sensor device 10, a potential of approximately 50 volts (V) is supplied from the power supply part 11 to the detecting electrodes 2 and then a leakage current caused by this potential is detected. The resistance between the detecting electrodes 2 is detected from the value of the leakage current. For example, the resistance between the detecting electrodes 2 is measured by an external measurement detection circuit (not shown). Alternatively, a circuit for measurement of the resistance between the detecting electrodes 2 (not shown) may be located on the insulating substrate 1.

For example, in a soot detection circuit, the power supply part 11 corresponds to the terminals electrically connected to an external power supply (not shown) as well as a rectifier, a transforming circuit, and the like, which constitute a part for receiving a predetermined electric power transmitted from the external power supply. The transmitted electric power is adjusted by the power supply part 11 into an electric power having a suitable condition for the measurement of the resistance between the detecting electrodes 2 and then transmitted to the detecting electrodes 2.

For example, the electrical connection between the power supply part 11 and the detecting electrodes 2 is established through the connection pads 5 and the internal wirings 3 described above. Here, in FIG. 1, connection conductors such as electrically conductive connection materials for electrically connecting the power supply part 11 to the connection pads 5 are schematically indicated by an imaginary line (a double-dotted dashed line).

The sensor device 10 according to the embodiment mentioned above includes the sensor board 4 having the above-mentioned configuration and hence has a high accuracy of detection. For example, in the case where the detecting electrodes 2 are formed of platinum and the temperature of the atmosphere (an exhaust gas) where particulates of soot are to be detected is approximately 550° C., the soot is decomposed by the catalytic reaction of platinum and hence the soot is not effectively detected. In contrast, in the case of the sensor board 4 according to the embodiment, the detecting electrodes 2 are catalytically inactive and hence decomposition of the soot is suppressed. Thus, the content ratio of the soot in the form of particulates is detected at a high accuracy.

MODIFIED EXAMPLES

Figure 4:
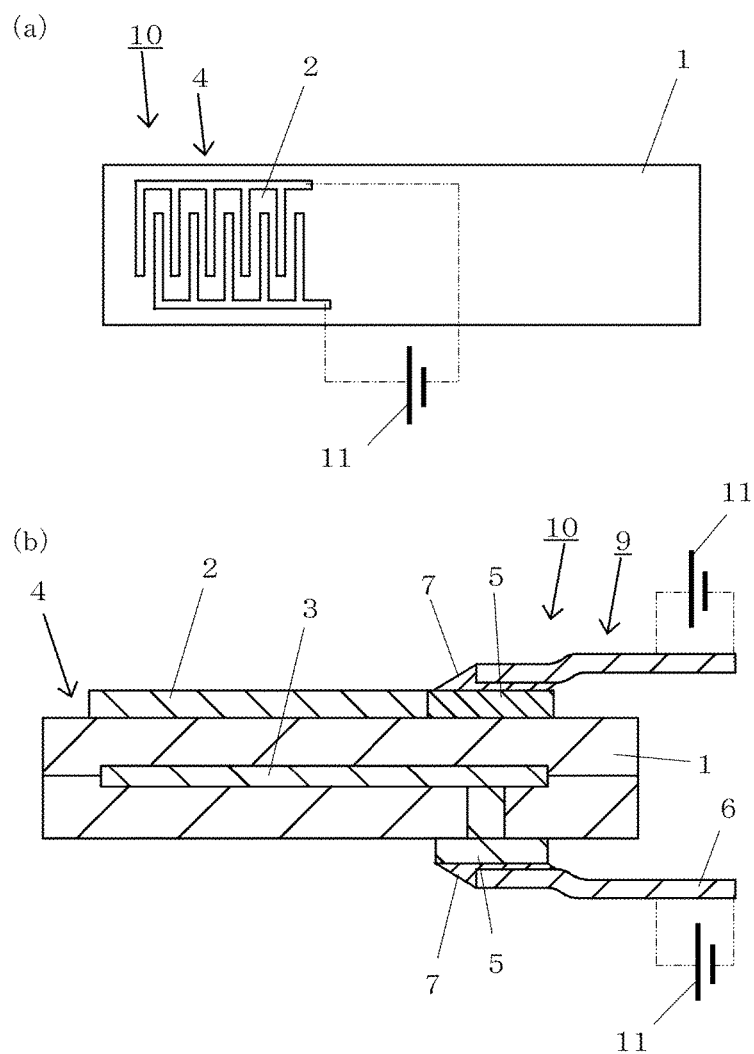
FIG. 4(a) is a top view showing a modified example of the sensor board and the sensor device shown in FIG. 1.
FIG. 4(b) is a sectional view showing another modified example of the sensor board and the sensor device shown in FIG. 1.

FIG. 4(a) is a top view showing a modified example of the sensor board 4 and the sensor device 10 shown in FIG. 1. FIG. 4(b) is a sectional view showing another modified example of the sensor board 4 and the sensor device 10 shown in FIG. 1. In FIG. 4, like parts to those in FIGS. 1 and 3 are designated by like reference numerals.

First Modified Example

In the example shown in FIG. 4(a), the detecting electrode 2 is in a comb shaped pattern. Further, the two detecting electrodes 2 are located in a positional relation of engaging with each other. In this case, for example, in a state where the size of the insulating substrate 1 in a plan view is suppressed as small as possible, a large length of the portion contributing to the detection in the detecting electrode 2 can be ensured. When a larger length of the portion contributing to the detection in the detecting electrode 2 is ensured, larger change in the resistance between the detecting electrodes 2 can be obtained. Further, the detection of particulates in the gas becomes easy. That is, even when the content of particulates in the gas is small, the particulates can more reliably be detected.

Thus, in this case, the sensor board 4 and the sensor device 10 can be provided which are more advantageous from the perspectives of the improvements in the accuracy and the sensitivity of detection of particulates in the gas and the size reduction in plan view.

Here, in FIG. 4(a), conductors such as the connection pads 5 for electrically connecting the power supply part 11 to the detecting electrodes 2 are schematically indicated by an imaginary line (a double-dotted dashed line).

Second Modified Example: Lead-Bearing Sensor Board

In the example shown in FIG. 4(b), the lead terminal 6 is joined to each of the connection pads 5 on the upper surface and the lower surface of the insulating substrate 1 so that a lead-bearing sensor board 9 is formed. For example, the lead terminal 6 is joined to the connection pad 5 via the above-mentioned joining layer 7.

In this case, an end part of the lead terminal 6 opposite to the end part joined to the connection pad 5 is joined and electrically connected to a predetermined location of the external electric circuit. That is, the electrical and mechanical connection of the sensor board 4 (the sensor device 10) to the external electric circuit is established through the lead terminal 6. The electrodes (such as the positive electrode and the negative electrode) different from each other in the power supply part 11 are connected to the lead terminals 6 different from each other. In the case where the mechanical connection between the sensor board 4 and the external electric circuit is established through the lead terminals 6, a stress such as a thermal stress caused by a thermal expansion difference between the insulating substrate 1 of the sensor board 4 and an external board (not shown) such as a resin substrate on which the external electric circuit is disposed, is relaxed more easily by virtue of elastic deformation of the lead terminals 6. Thus, in this case, the sensor board 4 and the sensor device 10 can be provided which are advantageous in the improvement or the like of the reliability of the external connection.

Similarly to the connection pad 5, the lead terminal 6 is not a part for detecting the particulates. Thus, the material used for forming the lead terminal 6 may be suitably selected in accordance with the environment of usage and a condition such as the productivity and the economic efficiency of the sensor board 4. For example, in the case where the lead terminal 6 is formed of a metallic material having excellent oxidation resistance such as platinum or gold, an advantage is obtained from the perspective of the reliability as the sensor device 10. Further, when importance is imparted to the economic efficiency or the like, the lead terminal 6 may be formed of an iron-based alloy such as an iron-nickel-cobalt alloy or, alternatively, copper or the like. Further, in the case where the lead terminal 6 is formed of an iron-based alloy, the exposed surface thereof may be protected by a plating layer such as a gold plating layer.

For example, the joining of the lead terminal 6 to the connection pad 5 may be achieved by using a brazing material (not shown) such as a silver solder (a silver-copper brazing material) or a gold solder in place of the joining layer 7. Similarly to the lead terminal 6, the brazing material is also suitably selected in accordance with various conditions at the time of manufacture or usage of the sensor board 4.

Here, in the case where the lead terminal 6 is to be joined to the connection pad 5, as the material for joining the connection pad 5 to the lead terminal 6, the joining layer 7 is employed when the strength of joining of the material to the connection pad 5, the workability, the economic efficiency, and the like are taken into consideration. For example, as in the example in FIG. 4(b), the sensor board 4 according to the second embodiment is employed as the sensor board 4. In other words, as the material used for joining the lead terminal 6 to the connection pad 5, the joining layer 7 (having melted and then solidified) of the second embodiment is suitable in practice.

In the sensor board 4 according to the second embodiment, the joining layer 7 is disposed on the connection pad 5. Thus, the lead terminal 6 can easily and firmly be joined to the connection pad 5 via the joining layer 7.

In the lead-bearing sensor board 9, the individual components (such as iron, chromium, and aluminum) of the second metallic material are melted by heating at the time of brazing of the lead terminal 6 and, after that, solidified and recrystallized. Thus, in the joining layer 7, the iron-chrome based alloy and the additive material such as aluminum are distributed substantially uniformly to each other in a polycrystalline structure.

Further, the connection pad 5 may extend from the lower surface of the insulating substrate 1 to the side surface (the end surface). Further, the lead terminal 6 may be disposed on an exposed surface other than the lower surface of the insulating substrate 1.

Further, the joining layer 7 may be employed for joining of the lead terminal 6 in the connection pad 5 on any one alone of the upper surface and the lower surface of the insulating substrate 1. Further, the lead terminal 6 may be arranged on any one alone of the upper and the lower surface.

Examples

Sensor boards of examples and sensor boards of comparative examples each provided with the detecting electrodes having the composition listed in Table 1 were manufactured and then the detection accuracy for particulates of soot in a gas was individually checked. In each example, the detecting electrode had a comb shaped pattern whose line width and gap (the interval of adjacent lines) were approximately 100 μm each. In the composition in Table 1, each numerical value following the element name indicates the content ratio (mass %) of the element in the detecting electrode.

The detection accuracy for soot was evaluated by a method that: each sensor board is set in a passage through which a gas containing a predetermined content ratio of soot flows; then the content ratio of the soot is measured; and then the measurement result (experimental value) is compared with the above-mentioned predetermined content ratio (theoretical value). As the soot in this method, soot contained in an exhaust gas from a diesel engine was employed. Further, the soot content in the gas was set to be approximately 10 mg/m$^3$.

In the sensor board of each example, the detecting electrodes were formed by using a base-metal based material of the composition listed in Table 1 (Experiment Nos. 3 to 9 and 11). Then, firing was performed in an atmosphere containing oxygen so that the passivation film was formed. In the sensor board of each comparative example, the detecting electrodes were formed by using a metallic material of single composition listed in Table 1 (Experiment Nos. 1 and 2). Further, in the sensor board of other comparative examples (Experiment Nos. 10 and 12), firing was performed in a reducing atmosphere so as not to form the passivation film.

In each detecting electrode having been prepared, electron probe microanalyzer (EPMA) analysis was performed on the surface portion of the detecting electrode so that the presence or absence of the passivation film was checked.

In the individual sensor boards of the implementation examples and the comparison examples, detection of soot in the above-mentioned gas was performed at the temperatures listed in Table 1. In the results of detection, data in which the ratio (experimental value/theoretical value) of the experimental value of the content of soot in the gas to the above-mentioned theoretical value falls within a range from 0.8 to 1.2 was regarded as passed (Passed). Further, data having a value smaller than 0.8 or greater than 1.2 was regarded as failed (Failed). Further, data in which the experimental value/theoretical value falls within a range from 0.9 to 1.1 was regarded as excellent (Excellent).

As a result, in Experiment Nos. 3 to 9 and 11 in which iron, nickel, and chromium serving as a base-metal based material were contained and the passivation film has been provided, it has been checked that the detection accuracy for soot was satisfactory even for a high temperature gas of approximately 600° C. In contrast, in Experiment Nos. 1, 2, 10, and 12 in which the passivation film was not provided, the detection accuracy for soot was degraded at gas temperatures of 400° C. or higher and hence was judged as failed. Here, in Sample Nos. 2 (detecting electrodes formed of tungsten), 10, and 12, progression of oxidation was recognized in the detecting electrodes and hence the detection accuracy has been degraded. Further, in Sample No. 1 (detecting electrodes formed of platinum), oxidation of the detecting electrodes was not recognized but the detection accuracy has been degraded. The reason of this was supposed that decomposition of soot was progressed by a catalytic action of platinum in the high temperature environment.

Further, the detecting electrodes of the compositions of Sample Nos. 7 to 9 and 11 had especially high detection accuracies. In these examples, the iron content ratio was 8 to 50 mass % (in particular, approximately 50 mass %), the nickel content ratio was approximately 28 to 76 mass % (in particular, approximately 30 mass %), and the chromium content ratio was 16 to 20 mass % (in particular, approximately 20 mass %). In the case where the nickel content ratio had a relatively small value of approximately 30 mass % (approximately 28 to 30 mass %), a high detection accuracy was obtained in an example that iron was set to be approximately 50 mass % (approximately 48 to mass %) and chromium was set to be approximately 20 mass % (approximately 19 to 20 mass %).

In the case where the nickel content ratio had a relatively large value of approximately 76 mass %, a high detection accuracy was obtained in an example that the iron was set to be approximately 8 mass % and chromium was set to be approximately 16 mass %. Further, a high detection accuracy was obtained also in the case where iron, nickel, and chromium fall within the above-mentioned ranges and that approximately 5 mass % of titanium or aluminum was further contained.

TABLE 1

| Experiment No. | Composition (mass %) | Passivation film | Experiment result (gas temperature) (° C.) | | | | | |
|---|---|---|---|---|---|---|---|---|
| | | | 20 | 100 | 300 | 400 | 500 | 600 |
| 1 | Pt | Absent | Excellent | Excellent | Excellent | Excellent | Failed | Failed |
| 2 | W | Absent | Excellent | Excellent | Excellent | Failed | Failed | Failed |
| 3 | Fe60Ni20Cr20 | Present | Excellent | Excellent | Excellent | Passed | Passed | Passed |
| 4 | Fe70Ni10Cr20 | Present | Excellent | Excellent | Excellent | Passed | Passed | Passed |
| 5 | Fe5Ni90Cr5 | Present | Excellent | Excellent | Excellent | Passed | Passed | Passed |
| 6 | Fe20Ni75Cr5 | Present | Excellent | Excellent | Excellent | Passed | Passed | Passed |
| 7 | Fe8Ni76Cr16 | Present | Excellent | Excellent | Excellent | Excellent | Excellent | Excellent |
| 8 | Fe50Ni30Cr20 | Present | Excellent | Excellent | Excellent | Excellent | Excellent | Excellent |
| 9 | Fe48Ni28Cr19Ti5 | Present | Excellent | Excellent | Excellent | Excellent | Excellent | Excellent |
| 10 | Fe46Ni27Cr17Ti10 | Absent | Excellent | Excellent | Passed | Failed | Failed | Failed |
| 11 | Fe48Ni28Cr19Al5 | Present | Excellent | Excellent | Excellent | Excellent | Excellent | Excellent |
| 12 | Fe46Ni27Cr17Al10 | Absent | Excellent | Excellent | Passed | Failed | Failed | Failed |

REFERENCE SIGNS LIST

1: Insulating substrate
2: Detecting electrode
21: Exposed surface (of Detecting electrode)

2a: Passivation film
3: Internal wiring
4: Sensor board
5: Connection pad
51: Exposed surface of Connection pad
6: Lead terminal
7: Joining layer
9: Lead-bearing sensor board
10: Sensor device
11: Power supply part

The invention claimed is:

1. A sensor board, comprising:
an insulating substrate having a principal surface;
a detecting electrode disposed on the principal surface of the insulating substrate, the detecting electrode being formed mainly of a first metallic material composed of a base-metal based material which is catalytically inactive with respect to a decomposition reaction of particulates;
a connection pad disposed on the principal surface of the insulating substrate and connected to the detecting electrode, the connection pad being formed of a same metallic material as that of the detecting electrode; and
a heater which is disposed inside the insulating substrate and heats the detecting electrode, the heater being composed mainly of the first metallic material,
the first metallic material being composed mainly of an iron-chromium alloy,
an exposed surface of the detecting electrode being covered by a passivation film of the first metallic material,
a joining layer being disposed on at least part of an exposed surface of the connection pad, and
the joining layer being formed of a second metallic material which contains, as a main component, a same metallic material as that of the connection pad and further contains aluminum as an additive material.

2. The sensor board according to claim 1, wherein the passivation film of the first metallic material has a uniform thickness over an entirety of the exposed surface of the detecting electrode.

3. The sensor board according to claim 1, wherein the joining layer is provided so as to extend from the exposed surface of the connection pad to the principal surface of the insulating substrate.

4. A lead-bearing sensor board, comprising:
the sensor board according to claim 1; and
a lead terminal joined to the detecting electrode via the joining layer.

5. A sensor device, comprising:
the sensor board according to claim 1; and
a power supply part which supplies a potential to the detecting electrode.

6. The sensor board according to claim 1,
wherein the connection pad contains aluminum, and a content ratio of aluminum in the joining layer is higher than a content ratio of aluminum in the connection pad by 0.1 to 5.0 mass %.

7. The sensor board according to claim 1,
wherein a content ratio of the additive material in the second metallic material is 0.1 to 5.0 mass parts in outside addition relative to 100 mass parts of the iron-chromium alloy.

8. The sensor board according to claim 1,
wherein a surface of the heater is provided with the passivation film of the first metallic material.

* * * * *